United States Patent
Radicke et al.

(10) Patent No.: US 11,948,689 B2
(45) Date of Patent: Apr. 2, 2024

(54) INDIVIDUAL DETERMINATION OF BREAST COMPRESSION IN MAMMOGRAPHY WITH ARTIFICIAL INTELLIGENCE

(71) Applicant: Siemens Healthcare GmbH, Erlangen (DE)

(72) Inventors: Marcus Radicke, Veitsbronn (DE); Madeleine Hertel, Forchheim (DE); Christian Huemmer, Lichtenfels (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 365 days.

(21) Appl. No.: 17/480,213

(22) Filed: Sep. 21, 2021

(65) Prior Publication Data
US 2022/0102002 A1 Mar. 31, 2022

(30) Foreign Application Priority Data
Sep. 28, 2020 (DE) .................. 10 2020 212 205.9

(51) Int. Cl.
*A61B 6/00* (2006.01)
*A61B 6/04* (2006.01)
(Continued)

(52) U.S. Cl.
CPC ........... *G16H 50/20* (2018.01); *A61B 6/0414* (2013.01); *A61B 6/502* (2013.01); *A61B 6/58* (2013.01);
(Continued)

(58) Field of Classification Search
None
See application file for complete search history.

(56) References Cited

U.S. PATENT DOCUMENTS

| 5,335,257 A | 8/1994 | Thunberg |
| 2008/0043904 A1 | 2/2008 | Hoernig |

(Continued)

FOREIGN PATENT DOCUMENTS

| DE | 102006038163 A1 | 2/2008 |
| DE | 102018200108 A1 | 7/2019 |

(Continued)

OTHER PUBLICATIONS

Christopher M. Bishop; "Neural Networks for Pattern Recognition"; Department of Computer Science and Applied Mathematics, Aston University Birmingham, UK; Clarendon Press—Oxford; 1995; 1995.

(Continued)

*Primary Examiner* — Hoon K Song
(74) *Attorney, Agent, or Firm* — Harness, Dickey & Pierce, P.L.C.

(57) ABSTRACT

A method is for determining a patient-adjusted breast compression in mammography. In an embodiment of the method, input data including individual, person-related data of a female patient, is determined. Furthermore, an adjusted individual compression point is determined by applying a function, trained by an algorithm based on machine learning, to the input data. The adjusted individual compression point is generated as the output data. Other embodiments include a method for providing a trained function; a breast compression determining device; a training device; and a mammography system.

25 Claims, 3 Drawing Sheets

(51) Int. Cl.
  *A61B 6/50* (2024.01)
  *A61B 6/58* (2024.01)
  *G16H 10/60* (2018.01)
  *G16H 40/40* (2018.01)
  *G16H 40/60* (2018.01)
  *G16H 50/20* (2018.01)
  *G16H 50/30* (2018.01)

(52) U.S. Cl.
  CPC ............ *G16H 10/60* (2018.01); *G16H 40/40* (2018.01); *G16H 40/60* (2018.01); *G16H 50/30* (2018.01)

(56) References Cited

U.S. PATENT DOCUMENTS

| | | |
|---|---|---|
| 2013/0028373 A1 | 1/2013 | Den Heeten et al. |
| 2014/0328458 A1 | 11/2014 | Erhard et al. |
| 2015/0327829 A1 | 11/2015 | Morita |
| 2016/0166217 A1 | 6/2016 | Davis et al. |
| 2019/0209106 A1 | 7/2019 | Bechtold et al. |
| 2020/0060632 A1 | 2/2020 | Blaski et al. |
| 2020/0261045 A1* | 8/2020 | Arai ........................ A61B 6/545 |
| 2020/0360312 A1 | 11/2020 | Hall et al. |
| 2022/0101984 A1* | 3/2022 | Park ........................ G16H 30/20 |

FOREIGN PATENT DOCUMENTS

| | | |
|---|---|---|
| ER | 2536336 B1 | 6/2014 |
| WO | WO 2019145896 A1 | 8/2019 |

OTHER PUBLICATIONS

German Office Action dated May 19, 2021.

\* cited by examiner

INDIVIDUAL DETERMINATION OF BREAST COMPRESSION IN MAMMOGRAPHY WITH ARTIFICIAL INTELLIGENCE

PRIORITY STATEMENT

The present application hereby claims priority under 35 U.S.C. § 119 to German patent application number DE 102020212205.9 filed Sep. 28, 2020, the entire contents of which are hereby incorporated herein by reference.

FIELD

Example embodiments of the invention generally relate to a method for determining a patient-adjusted breast compression in mammography, to a method for providing a trained function, to a breast compression determining device, to a training device and to a mammography system.

BACKGROUND

Mammography continues to play an important role in the early detection of breast carcinoma. In conventional mammography, an X-ray image is created of the female breast. The X-ray images are viewed at a special mammography diagnostic workstation, which comprises one or two gray scale monitors, with which the X-ray images are visually depicted. FIG. 1 shows an arrangement for two-dimensional mammography. To be able to identify lesions on the images, the breast tissue to be depicted has to be compressed. However, sub-optimum parameters are often conventionally chosen for breast compression. Conventional examination equipment often specifies only the parameters "compression force" and the "currently compressed breast thickness" for the user. Even more parameters have to be considered for a patient-adjusted compression, however, such as the tissue density, in other words the elastic properties of the breast, and the area of the breast. Since these additional parameters are not known in conventional procedures only an underdetermined system of equations can conventionally be constructed for calculation of an optimum compression of the breast, so a clear solution cannot be found. However, a sub-optimum breast compression often leads to a sub-optimal image quality or is associated with pain for the female patient being examined.

U.S. Pat. No. 5,335,257 A describes a method for the adjustment of the breast compression, with which a value for the compression is determined. However, in this case only the change over time in the compression force and thickness is considered and there is a reaction if the ratio of the change in the compression force and the change in the compression thickness exceeds a preset value.

EP 2 536 336 B1 describes a compression paddle with a plurality of spatially resolved capacitive pressure sensors, which measure the pressure really applied to the breast and make it available for a compression regulation.

DE 10 2018 200 108 A1 describes a method for the positioning of an examination object in respect of an X-ray machine in which image acquisitions from a camera are used to correctly position the breast and to estimate the size of the breast area.

SUMMARY

At least one embodiment of the present invention is directed to developing a better-adjusted breast compression for a mammography method with a good image quality and adequate comfort for the female patient.

Embodiments of the application are directed to a method for determination of a patient-adjusted breast compression in mammography, a method for providing a trained function, a breast compression determining device, a training device and a mammography system.

In at least one embodiment of the inventive method for determining a patient-adjusted breast compression in mammography, input data is determined, which comprises individual, person-related data of a female patient. Furthermore, an adjusted individual compression point is determined by applying a function, which was trained by an algorithm based on machine learning, to the input data, wherein the adjusted individual compression point is generated as the output data. The "adjusted individual" compression point should be taken to mean a compression point at which, on the one hand, predetermined demands for a minimum image quality are met and, on the other hand, a predetermined minimum level of patient comfort, which can depend on individual properties of a patient's breast and the subjective perception of a female patient, is achieved. The two demands can be individually established depending on the intended application.

In the inventive method of at least one embodiment, for providing a trained function, which can be used for at least one embodiment of the inventive method for determining a patient-adjusted breast compression in mammography, input training data is received, which comprises individual, person-related data of persons in a training database. Output training data, which is assigned to the input training data, is also received, wherein the output training data comprises an individually adjusted candidate compression point. Furthermore, a function is trained by an algorithm based on machine learning based upon the input data and the output data. Advantageously, no complex modeling approach has to be laboriously constructed for determination of the function, instead the function is automatically generated based upon the existing database of training data. It is in particular with a large number of different parameters that should be taken into account that such a procedure is superior to the purely model-based approach.

The inventive breast compression determining device of at least one embodiment has an input data determining unit for determining input data, which comprises individual, person-related data of a female patient. The inventive breast compression determining device also comprises a compression point determining unit for determining an adjusted individual compression point by applying a function, which was trained by an algorithm based on machine learning, to the input data, wherein the adjusted individual compression point is generated as the output data. In addition, the inventive breast compression determining device comprises a second interface for outputting the determined adjusted individual compression point. The inventive breast compression determining device shares the advantages of the inventive method for determining the breast compression of a female patient in mammography.

The inventive training device of at least one embodiment, which can be used to implement the training of the function based on machine learning used in the breast compression determining device of at least one embodiment has a first training interface for receiving input training data, which comprises individual, person-related data of persons in a training database. The inventive training device of at least one embodiment also comprises a second training interface for receiving output training data, which is assigned to the input training data, wherein the output training data comprises an individually adjusted candidate compression point. A training unit for training a function based on the training input data and the training output data, and an output interface for outputting the trained function is also part of the inventive training device of at least one embodiment. The inventive training device of at least one embodiment shares the advantages of the inventive training method of at least one embodiment.

The inventive mammography system of at least one embodiment features the inventive breast compression determining device of at least one embodiment and the inventive training device of at least one embodiment. The inventive mammography system of at least one embodiment combines the advantages of the breast compression determining device and the inventive training device of at least one embodiment.

The fundamental components of the inventive breast compression determining device of at least one embodiment and the inventive training device of at least one embodiment can be designed for the most part in the form of software components. This applies, in particular, to parts of the input data determining unit and the compression point determining unit of the breast compression determining device and the training unit of the training device.

An implementation largely in terms of software has the advantage that even previously used mammography devices can be easily adapted, possibly by retrofitting required hardware, by way of a software update in order to work inventively. In this regard the object is also achieved by a corresponding computer program product with a computer program, which can be loaded directly into a storage device of a mammography device and comprises program segments in order to carry out all steps of the inventive method of at least one embodiment when the computer program is run in the mammography device.

The inventive method of at least one embodiment for providing a trained function, comprises:
 receiving input training data, including individual, person-related data of persons in a training database;
 receiving output training data, assigned to the input training data, the output training data including an adjusted individual candidate compression point; and
 training a function by way of an algorithm based on machine learning based upon the input training data and the output training data.

The inventive training device breast compression determining device of at least one embodiment, comprises:
 an input data determining unit to determine input data, including individual, person-related data of a female patient;
 a compression point determining unit to determine an adjusted individual compression point by applying a function, trained by an algorithm based on machine learning, to the input data; and
 a second interface to output the determined adjusted individual compression point determined.

The inventive training device for a breast compression determining device of at least one embodiment, comprises:
 a first training interface to receive input training data including individual, person-related data of persons in a training database;
 a second training interface to receive output training data, assigned to the input training data, wherein the output training data includes an adjusted individual candidate compression point;
 a training unit to train a function based on the training input data and the training output data; and
 an output interface to output the trained function.

The inventive mammography system of at least one embodiment, comprises:
 the breast compression determining device of an embodiment; and
 a training device for the breast compression determining device, comprising:
  a first training interface to receive input training data including individual, person-related data of persons in a training database;
  a second training interface to receive output training data, assigned to the input training data, wherein the output training data includes an adjusted individual candidate compression point;
  a training unit to train the function based on the training input data and the training output data; and
  an output interface to output the trained function.

At least one embodiment is directed to an inventive non-transitory computer program product storing a computer program, directly storable to a storage device of a data processing device, including program segments to carry out the method of an embodiment when the computer program is run in the data processing device.

At least one embodiment is directed to an inventive non-transitory computer-readable medium, storing program segments, readable and runnable by an arithmetic unit, to carry out the method of an embodiment when the program segments are run by the arithmetic unit.

BRIEF DESCRIPTION OF THE DRAWINGS

The invention will be described and explained in more detail below with reference to the example embodiments represented in the figures.

In the drawings.

DETAILED DESCRIPTION OF THE EXAMPLE EMBODIMENTS

Figure 1:
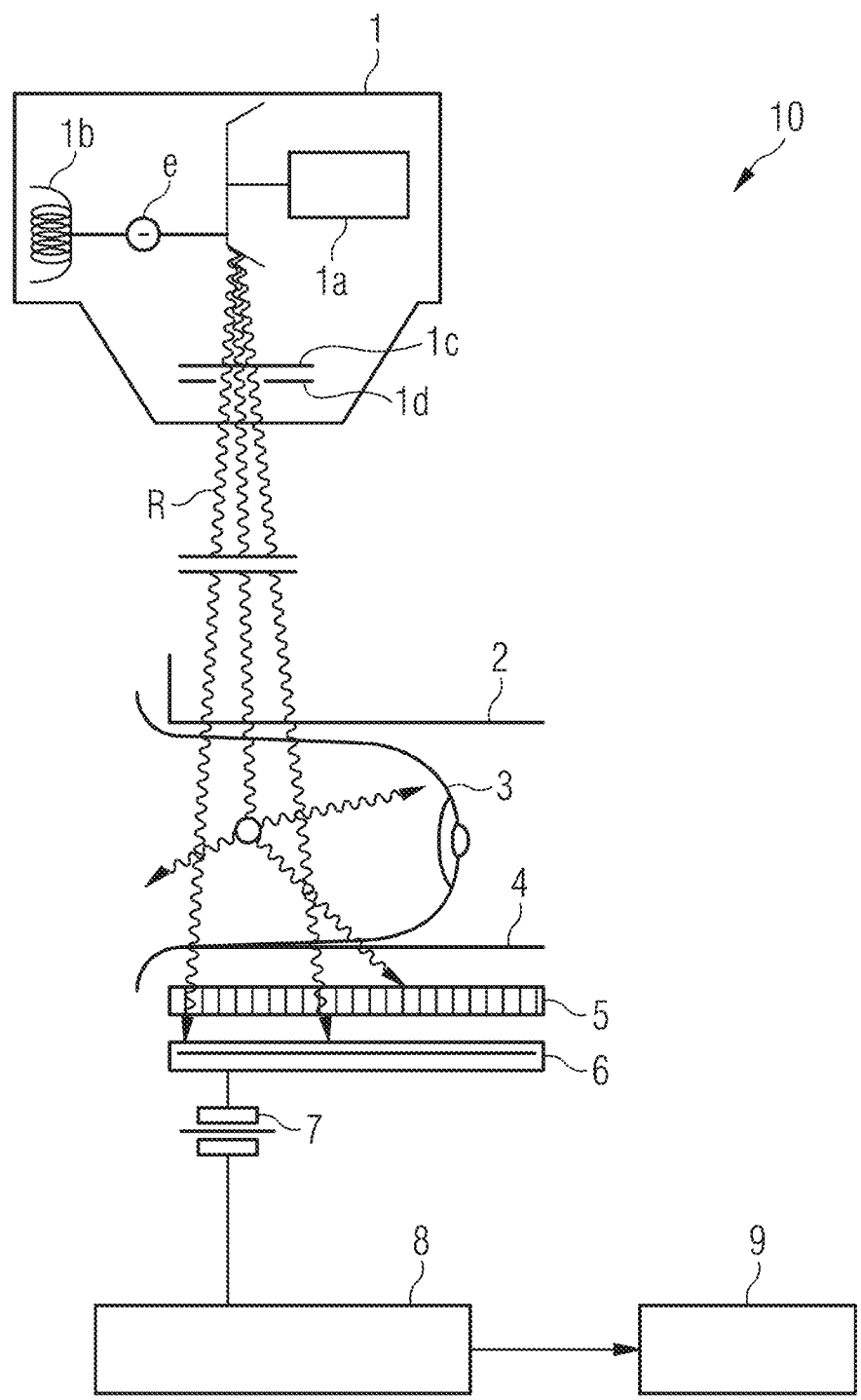
FIG. 1 shows a schematic representation of a mammography device.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

In at least one embodiment of the inventive method for determining a patient-adjusted breast compression in mammography, input data is determined, which comprises individual, person-related data of a female patient. Furthermore, an adjusted individual compression point is determined by applying a function, which was trained by an algorithm based on machine learning, to the input data, wherein the adjusted individual compression point is generated as the output data. The "adjusted individual" compression point should be taken to mean a compression point at which, on the one hand, predetermined demands for a minimum image quality are met and, on the other hand, a predetermined minimum level of patient comfort, which can depend on individual properties of a patient's breast and the subjective perception of a female patient, is achieved. The two demands can be individually established depending on the intended application.

Preferably, an optimum compression point is determined as the adjusted individual compression point for a female patient. An optimum compression point of this kind can, comprise, for example an optimum image quality with a predetermined minimum level of comfort that is still acceptable to the patient. Conversely, it can also comprise an optimum level of comfort with a predetermined minimum level of the quality of the image representation. Moreover, an optimum compression point of this kind can also be established such that an optimization of the two parameters takes place as a function of a previously established weighting of the parameters or of a previously established parameter value interval in which the two parameters should lie.

Advantageously, determining the individually adjusted compression point includes individual data of a person and a functional correlation between this individual data and the adjusted individual compression point. A function based on artificial intelligence can also take into account influencing variables that are difficult to model, such as the subjective pain perception of a person, in order to reach a compromise between a reasonable level of comfort for the patient and an adequate image quality.

In the inventive method of at least one embodiment, for providing a trained function, which can be used for at least one embodiment of the inventive method for determining a patient-adjusted breast compression in mammography, input training data is received, which comprises individual, person-related data of persons in a training database. Output training data, which is assigned to the input training data, is also received, wherein the output training data comprises an individually adjusted candidate compression point. Furthermore, a function is trained by an algorithm based on machine learning based upon the input data and the output data. Advantageously, no complex modeling approach has to be laboriously constructed for determination of the function, instead the function is automatically generated based upon the existing database of training data. It is in particular with a large number of different parameters that should be taken into account that such a procedure is superior to the purely model-based approach.

The algorithm based on machine learning is preferably based on an artificial neural feedforward network. The advantage of such a "feedforward network" is that it can map any complex mathematical correlations, and this is described, for example, in Bishop: Neural Networks for Pattern Recognition, 1995, the entire contents of which are hereby incorporated herein by reference.

In general there are three types of neural network:
convolutional networks: convolutional operators use local correlations, so the number of weights is reduced compared to "feedforward networks",
recurrent networks: feedback allows the acquisition of time-related correlations in sequential data,
"feedforward networks": all input variables are connected to all nodes in the next intermediate layer. These networks are primarily used when time- and location-related correlations of the input variables do not exist or are unknown, as is the case with the scenario forming the basis of at least one embodiment the invention.

The inventive breast compression determining device of at least one embodiment has an input data determining unit for determining input data, which comprises individual, person-related data of a female patient. The inventive breast compression determining device also comprises a compression point determining unit for determining an adjusted individual compression point by applying a function, which was trained by an algorithm based on machine learning, to the input data, wherein the adjusted individual compression point is generated as the output data. In addition, the inventive breast compression determining device comprises a second interface for outputting the determined adjusted individual compression point. The inventive breast compression determining device shares the advantages of the inventive method for determining the breast compression of a female patient in mammography.

The inventive training device of at least one embodiment, which can be used to implement the training of the function based on machine learning used in the breast compression determining device of at least one embodiment has a first training interface for receiving input training data, which comprises individual, person-related data of persons in a training database. The inventive training device of at least one embodiment also comprises a second training interface for receiving output training data, which is assigned to the input training data, wherein the output training data comprises an individually adjusted candidate compression point. A training unit for training a function based on the training input data and the training output data, and an output interface for outputting the trained function is also part of the inventive training device of at least one embodiment. The inventive training device of at least one embodiment shares the advantages of the inventive training method of at least one embodiment.

The inventive mammography system of at least one embodiment features the inventive breast compression determining device of at least one embodiment and the inventive training device of at least one embodiment. The inventive mammography system of at least one embodiment combines the advantages of the breast compression determining device and the inventive training device of at least one embodiment.

The fundamental components of the inventive breast compression determining device of at least one embodiment and the inventive training device of at least one embodiment can be designed for the most part in the form of software components. This applies, in particular, to parts of the input data determining unit and the compression point determining unit of the breast compression determining device and the training unit of the training device.

Basically, these components can, however, also be implemented partly, in particular when especially fast calculations are needed, in the form of software-assisted hardware, for example FPGAs or the like. Similarly, the required interfaces can be designed as software interfaces, for example when it is only a matter of acceptance of data from other software components. However, they can also be designed as interfaces constructed in terms of hardware, which interfaces are actuated by suitable software.

An implementation largely in terms of software has the advantage that even previously used mammography devices can be easily adapted, possibly by retrofitting required hardware, by way of a software update in order to work inventively. In this regard the object is also achieved by a corresponding computer program product with a computer program, which can be loaded directly into a storage device of a mammography device and comprises program segments in order to carry out all steps of the inventive method of at least one embodiment when the computer program is run in the mammography device.

Apart from the computer program, a computer program product of this kind can optionally comprise additional elements, such as documentation and/or additional components, also hardware components, such as hardware keys (dongles, etc.) in order to use the software.

The methods can be reproducibly carried out, and so as to be less prone to errors, on different mammography devices by way of a software implementation.

A computer-readable medium, for example a memory stick, a hard drive or another transportable or permanently installed data carrier, on which the program segments of the computer program, which can be read and run by a data processing device, for example an arithmetic unit, are stored, can serve for transportation to the storage device of the mammography device and/or for storage on the mammography device. For this the arithmetic unit can have, for example, one or more cooperating microprocessors or the like.

The claims and the subsequent description each contain particularly advantageous embodiments and developments of the invention. In particular the claims of one category can also be developed analogously to the dependent claims of a different category. In addition, the various features of different example embodiments and claims can also be combined to form new example embodiments within the context of the invention.

The inventive method of at least one embodiment for determining a patient-adjusted breast compression in mammography can be designed as a multi-stage sequential method. Determining input data also comprises experimental determining of an individual candidate compression point, which comprises a value for a compression force and a compression thickness of a breast of an individual female patient. In this variant, determining an adjusted individual compression point features generating or determining a deviation from the individual candidate compression point as the output data. The adjusted compression point is then determined based upon the individual candidate compression point and the determined deviation. A candidate compression point is determined for generating the input data therefore, and this comprises a value for a compression force and a compression thickness of a breast of an individual patient. The candidate compression point is determined experimentally. A compression force is exerted on the breast of an individual female patient and a change in the thickness is determined as a function of the change in the compression force. The candidate compression point is reached when the gradient of thickness relative to the compression force falls below a predetermined threshold value. The candidate compression point comprises a value for a thickness of the breast of an individual female patient and a value, assigned to this thickness, of a force or compression force exerted on this breast.

The determined candidate compression point is then checked for whether it is suitable or even optimum for an individual female patient. This does not have to be the case since, for example, the patient's comfort is not also directly included in the experimental determination of the candidate compression point. For this, further input data is received in addition to the candidate compression point, and this comprises individual, person-related data. A function, which was trained by an algorithm based on machine learning, is then applied to the input data and the candidate compression point, wherein a deviation from the candidate compression point is generated as the output data. The pain perception and the image quality of the test person achieved at a particular level of pain play a decisive role in the training of the algorithm or of the applied function. Firstly, the pain intensity should be as low as possible. Secondly, an adequate image quality should be achieved, however. The deviation has values for a deviation of the thickness of the compressed breast from the thickness value of the candidate compression point and the force value of the candidate compression point.

Finally, a corrected compression point is determined based upon the candidate compression point and the determined deviation. In the simplest case, the deviation and the candidate compression point are simply added vectorially in order to obtain the corrected compression point.

Advantageously, the determination of the corrected compression point includes individual data of a person and a functional correlation between this individual data and a deviation from a purely experimentally calculated candidate compression point. As already mentioned, a function based on artificial intelligence can also take into account influencing variables that are difficult to model, such as the subjective pain perception of a person, in order to reach a compromise between a reasonable level of comfort for a female patient and an adequate image quality. Advantageously, a further parameter, the candidate compression point, may be added to the input data in this multi-stage sequential variant, so the accuracy of determination of an individually adjusted compression point can be improved.

Preferably, the input data in the inventive method of an embodiment for determining the breast compression of a female patient in mammography comprises at least one of the following types of data:
 person-related, individual data relating to the general condition of the female patient,
 person-related, individual physical data based on previous mammography examinations,
 functional data of the mammography device,
 person-related, individual physical supplementary data from external sources.

The data relating to the general condition of the female patient comprises physiological data, which was also acquired without data from previous examinations with the relevant mammography device. For example, this personal, physiological data comprises the age of the female patient, their BMI (Body Mass Index), the number of children of the female patient, their bra size, information about a pre-existing condition in the region of the breast, an estimated breast density or a maximum tolerable pressure on the breasts.

When details on the estimated breast density are available, they are also already categorized in BI-RADS-ACR. This data can be found in the mammography image or an ultrasound image acquired in addition to the preceding mammography.

Information about pre-existing conditions in the region of the breasts can comprise, for example, information about scarring, which occurs with breast surgery. Painful changes to the breast can reduce the pressure tolerance of the female patient. The data can be used to estimate the breast density or the proportion of glands and fatty tissues based upon known statistical breast density distributions as a function of these values, in particular of the age, BMI, the breast size and the number of children. The information about pre-existing conditions can, as already mentioned, be used to estimate the extent of tolerable pressure.

The person-related, physical data based on previous examinations comprises at least one of the following types of data:
 the applied compression force,
 the compression thickness,
 the breast area on the detector,
 the BI-RADS-ACR-value.

The value of the applied compression force can be used in connection with the breast area on the detector for calculation of the pressure on the breast of the female patient used in the preceding acquisitions and can be used as a validation and rough guide value. If the newly determined values of the compression parameters compression force and compression thickness deviate greatly from the previously used values, a warning can be output to the medical staff. However, with small breast sizes a great change in the compression parameters is to be expected, so an exception has to be made here. The BI-RADS-ACR categories provide, on the one hand, information about the finding (BI-RADS category) and on the other hand, about the density of the breast or how pronounced the involution of the breast is (ACR category). Determination of the volumetric breast density enables a plausible estimation of the elastic properties of the breast and, together with the changes in the breast estimated by the intelligent algorithm in the time between current acquisition and a priori data, thus enables an optimized, patient-indicated compression or breast fixing.

Functional data of the mammography device comprises apparatus information, such as the absolute and time-resolved compression force and the absolute and time-resolved compression thickness. Until now this data alone has been used for determination of the compression point. The inclusion of the person-related, individual data relating to the general condition of the female patient and referred to as a complementary parameter, and the person-related, individual physical data based on previous mammography examinations allows a compression setting that is heavily adjusted to an individual patient.

The person-related, individual physical supplementary data from external sources comprises, for example, the breast size of the female patient based upon an estimation by a medically qualified person, an estimated BI-RADS-ACR value, which was determined by palpation of the breast by a medically qualified person, a breast size, which was determined by a body scanner, also referred to as a "full-body scanner", and the patient's weight, which was determined by way of scales. This additional data can be used for verification of the other data or for the addition of new information as the basis for determination of a corrected compression point.

Different interpretation procedures can be applied to take account of the described four different types of data by the mapping function based on artificial intelligence. In a first procedure, at least some of the input data of different types of data, preferably all input data, is considered and weighted as if equal for this function, independently of the data source. With this approach there is, for example, a separate input of a neural network for each type of data. No analysis or interpretation prior to application of the AI algorithm is required with this variant.

Alternatively, different data can also be weighted according to its significance, so particular data has a greater influence on the AI algorithm. For example, types of data, for which only an incomplete database exists, can have a lower weighting, or data of different types of data can be allocated a shared value, which is then incorporated in the AI algorithm with an appropriately lower weight. This variant can be expedient, for example, when a complete data set does not exist for every female patient.

The correlations between different types of data can also be taken into account and data of different types of data can be combined according to a mapping rule in order to extract particularly relevant features for the AI-based function. For example, one single significant value respectively could be determined for each of the four different groups of data. For example, exactly one separate input respectively would then be allocated to each of the groups of data with application of an artificial neural network in order to generate the function. Advantageously, data processing is simplified by the AI-based function, so computing effort is reduced.

The choice of evaluation strategy can be achieved, for example, by way of a heuristic procedure, although it can also be achieved with modeling or by way of AI-based algorithms.

Particularly preferably, the input data determining unit of the inventive breast compression determining device has a candidate determining unit for determining a candidate compression point. The candidate compression point comprises a value for a compression force and a compression thickness of a breast of an individual patient, which can be determined by gradually increasing a compression force and determining a change in the thickness as a function of the change in the compression force.

The input data determining unit of the inventive breast compression determining device of at least one embodiment also comprises a first interface for receiving input data, which comprises individual, person-related data. In addition, the inventive breast compression determining device or, more precisely, the compression point determining unit, comprises a deviation determining unit for applying a function, which was trained by an algorithm based on machine learning, to the input data. A deviation from the candidate compression point is determined or generated as the output data in this case. A correction unit for determining a corrected or individually adjusted compression point based upon the candidate compression point and the determined deviation is also part of the inventive breast compression determining device or the compression point determining unit in this variant.

Advantageously, based upon a correction value determined based upon AI, the correction unit determines an adjusted compression point, which brings about improved patient comfort and/or improved image quality of a mammography image of an individual female patient.

FIG. 1 shows a schematic representation of a conventional mammography unit 10. The mammography unit 10 comprises an X-ray tube 1 with a rotating anode 1a and a cathode 1b, between which a tube voltage of 25 to 35 kV is generated. An X-ray beam R, which passes through a filter 1c and a diaphragm 1d with a light-beam localizer, is generated on a focal track. The X-ray beam R penetrates a compression paddle 2 and strikes the breast 3 to be examined. The X-ray beams are attenuated in the breast tissue. The attenuated X-ray beams then penetrate a supporting plate 4, are conducted through an anti-scatter grid 5, with which scatter radiation is removed, and finally strike a screen-film combination 6.

The screen-film combination 6 guarantees the representation of the finest structures in the mamma. For quality assurance an automatic exposure 8 is used in diagnostic radiology, with which an adjustment to the thickness, the density and the tube voltage used is made. The function of the automatic exposure is to attain a mean optical density of 1.2 to 1.6, as far as possible independently of the breast thickness and the breast density. The automatic exposure collaborates with a measuring chamber 7, which is arranged in the beam path below the cassette of the screen-film combination 6. The dose behind the cassette in a representative area is measured with the measuring chamber 7. Once the activation dose necessary for the chosen mean optical film density is reached, the automatic system cuts off the radiation. A generator 9 with a short switching time is controlled by the automatic exposure. The X-ray voltage is generated by the generator 9. The breast 3 is pressed and compressed against the supporting plate 4 with the aid of the compression paddle 2. The compression of the breast 3 improves the resolution by reducing the spacing of details remote from the screen in the mammary glands. The geometric blurring is also reduced thereby. Furthermore, the contrast is improved since primarily high-contrast, low-energy radiation is effective in the penetration of thinner layers of tissue. Furthermore, a clear dose reduction is achieved by the compression owing to the reduction in the breast thickness to be radiographed. The scattered radiation fraction is reduced by the compression, moreover, so the image contrast is improved. In addition, the compression allows the visualization of the smallest masses, since normal tissue may usually be spread apart by compression, in contrast to small malignant tumor masses. A further advantage is a reduction in the half-shade formation since, due to the reduced thickness of the breast 3, the spacing between a possible tumor in the breast 3 and the exposure film 6 is reduced.

Figure 2:
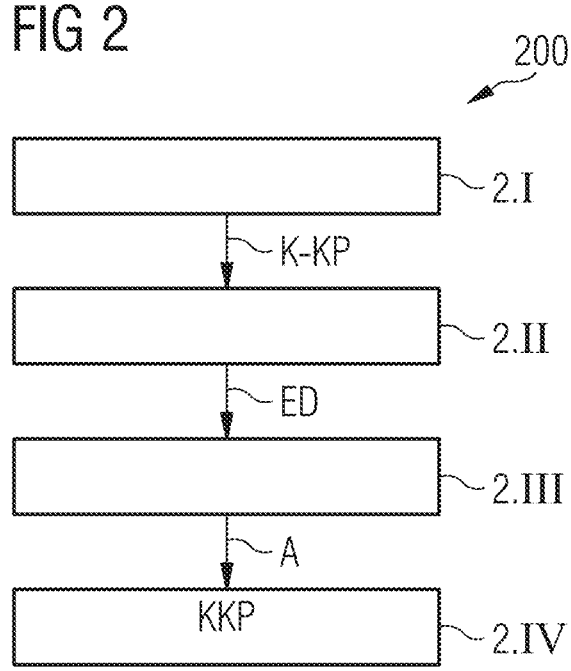
FIG. 2 shows a flowchart, which illustrates a method for determining a breast compression of a female patient in mammography according to one example embodiment of the invention.

FIG. 2 shows a flowchart 200 which illustrates a method for determining a breast compression of a female patient in mammography according to one example embodiment of the invention. In step 2.I, firstly a candidate compression point K-KP is determined. The candidate compression point K-KP comprises a two-dimensional vector, which comprises a value for a compression force and a compression thickness of a breast of an individual patient. This candidate compression point K-KP is determined before X-ray imaging by gradually increasing a compression force and determining a change in the thickness as a function of the change in the compression force. The compression force is increased until the gradient of the compression thickness after the compression force falls below a predetermined minimum value. But this candidate compression point K-KP can now have an excessively high value of a compression force if the compressed breast is particularly soft and is already greatly compressed at the candidate compression point K-KP, therefore, so the female patient is already experiencing great pain. On the other hand, the candidate compression point K-KP can also have an insufficient value of a compression force if the compressed breast is very hard and the breast is compressed only very slightly at the candidate compression point K-KP, therefore, so an adequate image quality would not be attained during a subsequent mammogram. A calibration, in other words a determination of a deviation A of a corrected compression point KKP from the candidate compression point K-KP, is accordingly necessary following the mechanical adjustment of the compression point. The demand for a minimum image quality and a minimum level of patient comfort should be met at the corrected compression point KKP. The minimum level of patient comfort is then attained if a compression pressure is lower than a pressure at which a pain threshold of a female patient is exceeded. The compression point can then be adjusted accordingly based upon the calibration value or calibration vector A.

Additional input data ED is acquired for calibration in step 2.II, therefore, which data comprises individual, person-related data. In this simple example embodiment, this input data ED comprises person-related, individual data relating to the general condition of the female patient, such as the age, the BMI and the number of children, as the individual, person-related data.

The input data can additionally also comprise person-related, individual physical data based on previous mammography examinations, functional data of the mammography device and person-related, individual physical supplementary data from external sources.

In step 2.III, a function based on a neural network is applied to the input data ED. The function maps the input data ED onto output data AD. The output data AD specifies a deviation A, determined by the function, from the candidate compression point K-KP. The deviation A is a vector, which specifies a deviation of the compression force and the compression thickness from the candidate compression point K-KP.

Finally, in step 2.IV, a corrected compression point KKP is determined based upon the candidate compression point K-KP and the determined deviation A. The two vectors of the candidate compression point K-KP and the deviation are simply added together in this case.

Figure 3:
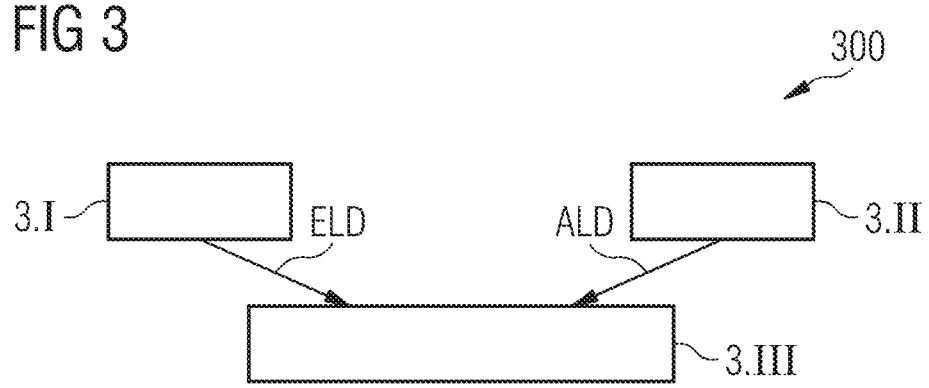
FIG. 3 shows a flowchart, which illustrates a training method, a method for providing a trained function for determination of a deviation from a candidate compression point, therefore, according to one example embodiment of the invention.

FIG. 3 shows a flowchart 300, which illustrates a training method, a method for providing a trained function for determination of a deviation from a candidate compression point K-K, therefore.

Figure 4:
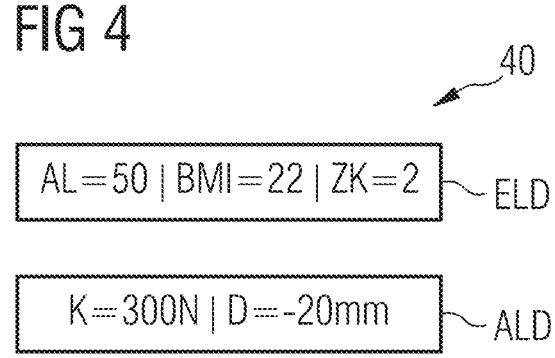
FIG. 4 shows a schematic representation of an individual training data set of an individual test person.

In step 3.I, firstly input training data ELD is received, for example from a database, which comprises individual, person-related data of persons in a training database. In the example embodiment illustrated in FIG. 3, this individual, person-related data features the age AL, the BMI (Body-Mass-Index) and the number ZK of children of a large number of test persons. FIG. 4 represents, by way of example, just one such set of input data ELD for a person.

Furthermore, in step 3.II, what is known as cabled output training data ALD assigned to the input training data ELD is received from the database. The output training data ALD is in each case assigned to the input training data ELD. In other words, the individual data sets of the output training data ALD, which are to be assigned to different test persons, are in each case assigned to the individual input training data sets ELD, which are associated with the respective test persons. The output training data ALD in each case has a deviation A from a candidate compression point K-KP.

Finally, in step 3.III, an artificial neural network is trained based upon the input training data ELD and the output training data ALD.

FIG. 4 shows a schematic representation of a single training data set 40 of a single test person with an input training data vector ELD and an output training data vector ALD. The input training data vector ELD comprises the age AL, the BMI and the number ZK of children of a test person, the output data training data vector ALD comprises deviation values A from a previously determined candidate compression point K-KP of a test person. In the example embodiment shown in FIG. 4, a test person is 50 years old, has a BMI von 22 and two children. The deviation A from a candidate compression point lies at an additional force K of +300 N and a reduced thickness D of −20 mm.

An artificial neural network may accordingly be trained based upon a large number of training data sets 40 of this kind in such a way that for any female patient to be examined, it determines a deviation A from a candidate compression point K-KP experimentally determined in advance.

Figure 5:
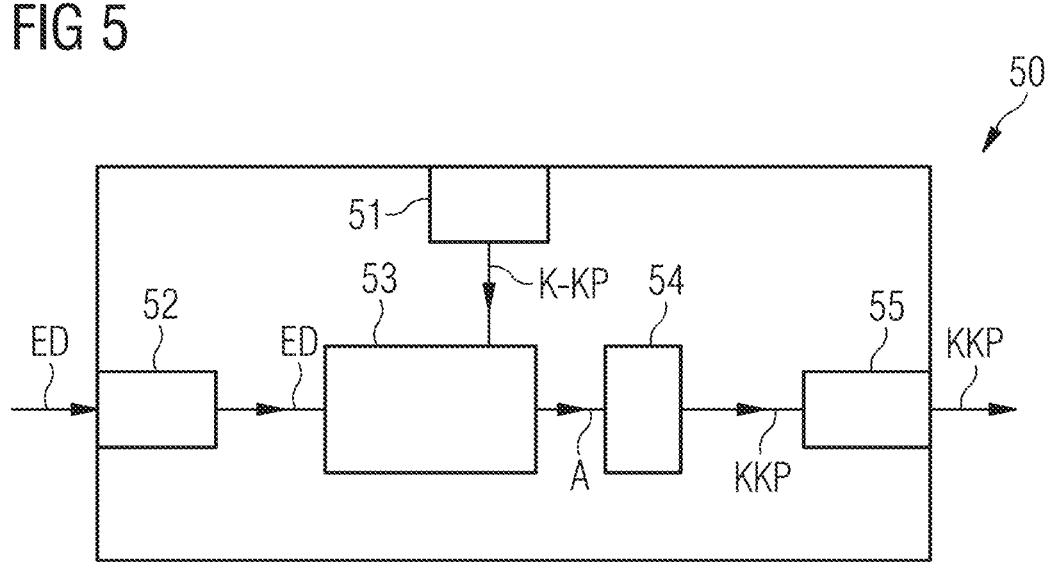
FIG. 5 shows a schematic representation of a breast compression determining device according to one example embodiment of the invention.

FIG. 5 schematically represents a breast compression determining device 50 according to one example embodiment of the invention. The breast compression determining device 50 comprises a candidate determining unit 51 for determining a candidate compression point K-KP. The candidate compression point K-KP comprises a value for a compression force and a compression thickness of a breast of an individual patient. A candidate compression point K-KP of this kind can be experimentally determined by gradually increasing a compression force and determining a change in the thickness or the spacing between the supporting plate 4 and the compression paddle 2 (see FIG. 1) as a function of the change in the compression force. Furthermore, the breast compression determining device 50 also comprises a first interface 52 for receiving input data ED, which comprises individual, person-related data. A deviation determining unit 53, which processes the input data ED by applying an artificial neural network to the input data ED, is also part of the breast compression determining device 50. Output data AD, which specifies a deviation A from the candidate compression point K-KP, is generated by the application of the artificial neural network. In addition, the breast compression determining device 50 also comprises a correction unit 54, which determines a corrected compression point KKP based upon the candidate compression point K-KP and the determined deviation A. Furthermore, the breast compression determining device 50 comprises a second interface 55 for outputting the determined corrected compression point KKP.

Figure 6:
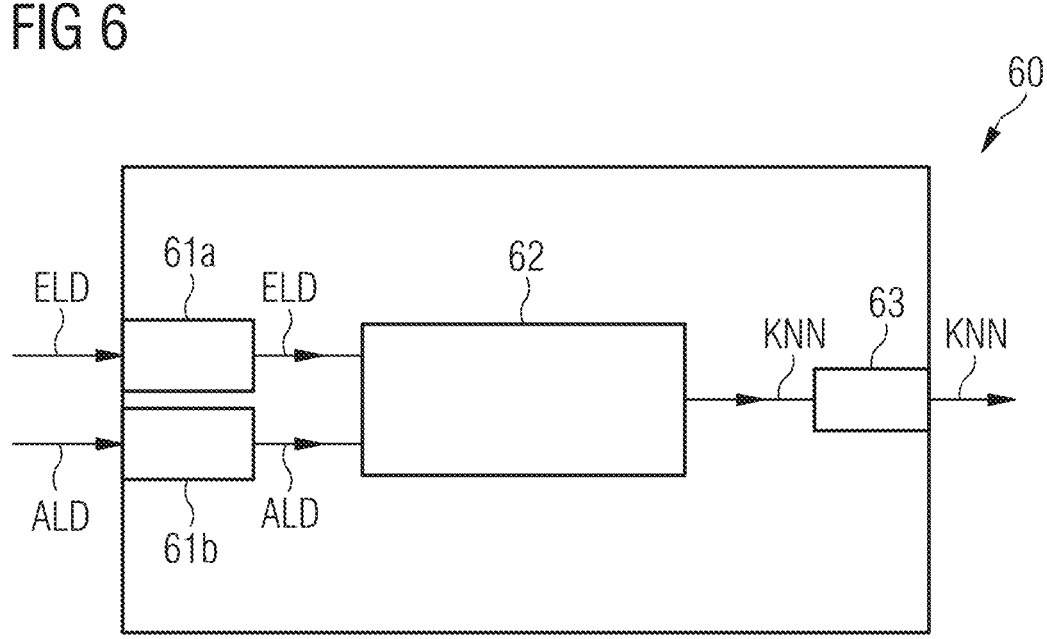
FIG. 6 shows a schematic representation of a training device according to one example embodiment of the invention.

FIG. 6 schematically represents a training device 60 according to one example embodiment der invention. The training device 60 comprises a first training interface 61a for receiving input training data ELD, which comprises individual, person-related data of persons in a training database (not shown), and a second training interface 61b for receiving output training data ALD, which is assigned to the input training data ELD, wherein the output training data ALD comprises a deviation A from a candidate compression point K-KP. The training device 60 also comprises a training unit 62, which is adapted to train an artificial neural network based on the training input data ELD and the training output data ALD. Furthermore, the training device 60 also comprises an output interface 63 for outputting the generated artificial neural network KNN to a breast compression determining device 50 or the deviation determining unit 53 of the breast compression determining device 50 (see FIG. 5).

In conclusion, reference is made one again to the fact that the above-described methods and devices are merely preferred example embodiments of the invention and that the invention can be varied by a person skilled in the art without departing from the scope of the invention insofar as it is specified by the claims. For the sake of completeness, reference is also made to the fact that use of the indefinite article "a" or "an" does not preclude the relevant features from also being present several times. Similarly, the term "unit" does not preclude this from comprising a plurality of components, which can optionally also be spatially distributed.

Of course, the embodiments of the method according to the invention and the imaging apparatus according to the invention described here should be understood as being example. Therefore, individual embodiments may be expanded by features of other embodiments. In particular, the sequence of the method steps of the method according to the invention should be understood as being example. The individual steps can also be performed in a different order or overlap partially or completely in terms of time.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining a patient-adjusted breast compression in mammography, comprising:
   determining input data including individual, person-related data of a female patient; and
   determining an adjusted individual compression point by applying a function, trained by an algorithm based on machine learning, to the input data, the adjusted individual compression point being generated as output data.

2. The method of claim 1, wherein the determining includes determining an optimum compression point for a female patient as the adjusted individual compression point.

3. The method of claim 1, wherein
   the determining of the input data includes experimental determining of an individual candidate compression point including a value for a compression force and a compression thickness of a breast of an individual female patient,
   the determining of the an adjusted individual compression point includes generating a deviation from the individual candidate compression point as the output data, and
   the determining of the adjusted individual compression point includes determining the adjusted individual compression point based upon the individual candidate compression point and the deviation generated.

4. The method of claim 1, wherein the input data includes at least one of:
   person-related, individual data relating to a general condition of the female patient,
   person-related, individual physical data based on previous mammography examinations,
   functional data of a mammography device, and
   person-related, individual physical supplementary data from external sources.

5. The method of claim 4, wherein the person-related, individual data relating to the general condition of the female patient includes at least one of:
   age,
   BMI,
   number of children,
   bra size,
   pre-existing condition in a region of a breast,
   estimated breast density, and
   maximum tolerable pressure.

6. The method of claim 4, wherein the person-related, physical data based on previous examinations includes at least one of:
   an applied compression force,
   a compression thickness,
   a breast area on a detector, and
   a BI-RADS-ACR value.

7. The method of claim 4, wherein the functional data of the mammography device used for mammography includes at least one of:
   an absolute compression force of the mammography device,
   a time-resolved compression force of the mammography device,
   an absolute compression thickness, and
   a time-resolved compression thickness.

8. The method of claim 4, wherein the person-related, individual physical supplementary data from external sources includes at least one of:
   breast size from an estimate by a medically qualified person,
   an estimated BI-RADS-ACR value, determined by palpation of a breast by a medically qualified person,
   a breast size, determined by a body scanner, and
   a weight of a patient, determined by scales.

9. The method of claim 1, wherein at least some of the input data of different types of data for the function
   is considered and weighted as if equal independently of a data source or
   is weighted according to significance or
   is combined according to a mapping rule.

10. A method for providing a trained function, comprising:
    receiving input training data, including individual, person-related data of persons in a training database;
    receiving output training data, assigned to the input training data, the output training data including an adjusted individual candidate compression point; and
    training a function by way of an algorithm based on machine learning based upon the input training data and the output training data.

11. The method of claim 10, wherein the algorithm based on machine learning is based on an artificial neural feed-forward network.

12. A breast compression determining device, comprising:
    an input data determining unit to determine input data, including individual, person-related data of a female patient;
    a compression point determining unit to determine an adjusted individual compression point by applying a function, trained by an algorithm based on machine learning, to the input data; and
    a second interface to output the determined adjusted individual compression point.

13. The breast compression determining device of claim 12,
wherein
the input data determining unit comprises:
a candidate determining unit to experimentally determine an individually adjusted candidate compression point, the individually adjusted candidate compression point including a value for a compression force and a compression thickness of a breast of an individual female patient, and
a first interface to receive input data, including individual, person-related data, and wherein
the compression point determining unit comprises:
a deviation determining unit to apply a function, trained by an algorithm based on machine learning, to the input data, wherein a deviation from a candidate compression point is generated as output data, and
a correction unit to determine an adjusted compression point based upon the candidate compression point and the deviation determined.

14. A training device for a breast compression determining device, comprising:
a first training interface to receive input training data including individual, person-related data of persons in a training database;
a second training interface to receive output training data, assigned to the input training data, wherein the output training data includes an adjusted individual candidate compression point;
a training unit to train a function based on the training input data and the training output data; and
an output interface to output the trained function.

15. A mammography system, comprising:
the breast compression determining device of claim 12; and
a training device for the breast compression determining device, comprising:
a first training interface to receive input training data including individual, person-related data of persons in a training database;
a second training interface to receive output training data, assigned to the input training data, wherein the output training data includes an adjusted individual candidate compression point;
a training unit to train the function based on the training input data and the training output data; and
an output interface to output the trained function.

16. A non-transitory computer program product storing a computer program, directly storable to a storage device of a data processing device, including program segments to carry out the method of claim 1 when the computer program is run in the data processing device.

17. A non-transitory computer-readable medium, storing program segments, readable and runnable by an arithmetic unit, to carry out the method of claim 1 when the program segments are run by the arithmetic unit.

18. The method of claim 2, wherein
the determining of the input data includes experimental determining of an individual candidate compression point including a value for a compression force and a compression thickness of a breast of an individual female patient,
the determining of the an adjusted individual compression point includes generating a deviation from the individual candidate compression point as the output data, and
the determining of the adjusted individual compression point includes determining the adjusted individual compression point based upon the individual candidate compression point and the deviation generated.

19. The method of claim 2, wherein at least some of the input data of different types of data for the function
is considered and weighted as if equal independently of a data source or
is weighted according to significance or
is combined according to a mapping rule.

20. The method of claim 1, wherein the function is produced by a method for providing a trained function, comprising:
receiving input training data, including individual, person-related data of persons in a training database;
receiving output training data, assigned to the input training data, the output training data including an adjusted individual candidate compression point; and
training a function by way of an algorithm based on machine learning based upon the input training data and the output training data.

21. A non-transitory computer program product storing a computer program, directly storable to a storage device of a data processing device, including program segments to carry out the method of claim 10 when the computer program is run in the data processing device.

22. A non-transitory computer program product storing a computer program, directly storable to a storage device of a data processing device, including program segments to carry out the method of claim 20 when the computer program is run in the data processing device.

23. A non-transitory computer-readable medium, storing program segments, readable and runnable by an arithmetic unit, to carry out the method of claim 10 when the program segments are run by the arithmetic unit.

24. A non-transitory computer-readable medium, storing program segments, readable and runnable by an arithmetic unit, to carry out the method of claim 20 when the program segments are run by the arithmetic unit.

25. The breast compression determining device of claim 12,
wherein the function is produced by a training device, comprising:
a first training interface to receive input training data including individual, person-related data of persons in a training database;
a second training interface to receive output training data, assigned to the input training data, wherein the output training data includes an adjusted individual candidate compression point;
a training unit to train a function based on the training input data and the training output data; and
an output interface to output the trained function.

* * * * *